United States Patent
Carola et al.

(10) Patent No.: US 9,382,224 B2
(45) Date of Patent: Jul. 5, 2016

(54) 7-ACYLOXYCHROMEN-4-ONE DERIVATIVES AND THE USE THEREOF AS SELF-TANNING SUBSTANCES

(75) Inventors: Christophe Carola, Bensheim (DE); Rene Peter Scheurich, Gross-Zimmern (DE)

(73) Assignee: MERCK PATENT GMBH, Darmstadt (DE)

( * ) Notice: Subject to any disclaimer, the term of this patent is extended or adjusted under 35 U.S.C. 154(b) by 129 days.

(21) Appl. No.: 13/980,067

(22) PCT Filed: Dec. 27, 2011

(86) PCT No.: PCT/EP2011/006574
§ 371 (c)(1),
(2), (4) Date: Jul. 17, 2013

(87) PCT Pub. No.: WO2012/097857
PCT Pub. Date: Jul. 26, 2012

(65) Prior Publication Data
US 2013/0287716 A1     Oct. 31, 2013

(30) Foreign Application Priority Data
Jan. 21, 2011   (DE) .................. 10 2011 009 112

(51) Int. Cl.
*C07D 311/22*   (2006.01)
*A61K 8/49*   (2006.01)
*A61Q 19/04*   (2006.01)

(52) U.S. Cl.
CPC .............. *C07D 311/22* (2013.01); *A61K 8/498* (2013.01); *A61Q 19/04* (2013.01)

(58) Field of Classification Search
CPC ....... A61K 8/498; A61Q 19/04; C07D 311/22
USPC ............................. 424/59; 549/401
See application file for complete search history.

(56) References Cited

U.S. PATENT DOCUMENTS

| | | | |
|---|---|---|---|
| 2004/0220137 A1 | 11/2004 | Sauermann | |
| 2007/0191305 A1* | 8/2007 | Carola et al. | 514/58 |
| 2009/0220438 A1 | 9/2009 | Carola et al. | |
| 2010/0158829 A1 | 6/2010 | Bajor et al. | |

FOREIGN PATENT DOCUMENTS

| | | | |
|---|---|---|---|
| DE | 10133202 A1 | | 1/2003 |
| JP | 09-188608 | * | 7/1997 |
| JP | 9188608 A | | 7/1997 |
| KR | 1995-39732 | * | 11/1995 |
| WO | 9304665 A1 | | 3/1993 |
| WO | 2007087956 A1 | | 8/2007 |

OTHER PUBLICATIONS

Tanaka et al.; Title: Chromone and chromanone glucosides from Hypericum sikokumontanum and their anti-Helicobacter pylori activities; Phytochemistry. Jan. 2009. issue; 70(1); pp. 141-6; Epub Dec. 31, 2008.*
Reddy et al; title: A convenient synthesis of 2-styrylchromones by teh modified Baker-Venkataraman trasfermation, Indian Journal of Chemistry, vol. 26b, pp. 974-976, published Oct. 1987.*
International Search Report from PCT/EP2011/006574 dated Mar. 19, 2012.
T. Hori et al. "Database WPI" Week 199739; Thomson Scientific, London, GB; XP-002668584; [1997]; 2 pages.
English Translation Abstract for WO9304665A1 dated Mar. 18, 1993.
T. Ross Kelly et al. "Synthesis of Schumanniophytine and Isoschumanniophytine" J. Org. Chem. [1992], vol. 57, pp. 1593-1597.
David A. Brown, "Skin Pigmentation Enhancers" Journal of Photochemistry and Photobiology, vol. 63, [2001], pp. 148-161.
Mitchell L. Schlossman, "Treated Pigments-New Ways to Impart Color on the Skin" Cosmetics & Toiletries, vol. 105, [Feb. 1990], pp. 53-64.
Katarzyna Lemanska et al., "Effect of substitution pattern on TEAC antioxidant activity of mono- and dihydroxyflavones" Current Topics in Biophysics, vol. 24, No. 2, [2000], pp. 101-108.
Catherine A. Rice-Evans et al., "Antioxidant properties of phenolic compounds" Trends in Plant Science, vol. 2, No. 4, [Apr. 1997], pp. 152-159.
Katarzyna Lemanska et al., "The influence of pH on antioxidant properties and the mechanism of antioxidant action of hydroxyflavones" Free Radical Biology & Medicine, vol. 31, No. 7, [2001], pp. 869-881.

* cited by examiner

*Primary Examiner* — Johann R Richter
*Assistant Examiner* — Yanzhi Zhang
(74) *Attorney, Agent, or Firm* — Millen White Zelano and Branigan, PC; John Sopp; Anthony Zelano

(57) ABSTRACT

The present invention relates to chromen-4-one derivatives of the formula (I), to the use thereof as self-tanning substance or for increasing melanin synthesis, improving melanin transport and/or improving the distribution of melanin in suprabasal layers, and to preparations comprising these chromen-4-one derivatives.

25 Claims, No Drawings

7-ACYLOXYCHROMEN-4-ONE DERIVATIVES AND THE USE THEREOF AS SELF-TANNING SUBSTANCES

The present invention relates to chromen-4-one derivatives of the formula I, to the use thereof as self-tanning substance or for increasing melanin synthesis, improving melanin transport and/or improving the distribution of melanin in suprabasal layers, and to preparations comprising these chromen-4-one derivatives.

The trend away from refined paleness towards "healthy, sporty brown skin" has been uninterrupted for years. In order to achieve a tanned complexion, people expose their skin to sunlight, since this causes pigmentation due to melanin formation. However, the UV radiation in sunlight also has a damaging effect on the skin. Besides acute damage (sunburn), long-term damage occurs on excessive irradiation with light from the UVB region (wavelength 280-320 nm), such as, for example, an increased risk of contracting skin cancer. Excessive exposure to UVB and UVA radiation (wavelength: 320-400 nm) generates highly reactive free-radical species, which multiply further even after termination of the irradiation, and wrinkling and skin ageing occur as a consequence thereof.

Tanning (pigmentation) of the skin offers natural protection against the adverse consequences of sunlight. The epidermis contains individual pigment-forming cells, the melanocytes, besides the basal cells in its lowest layer, the basal layer. UV light stimulates the production of melanin in these cells, which is transported into the keratinocytes (horny cells), where it becomes visible as a brown skin colour. Melanin protects the cell nuclei against further irradiation and the adverse effects it causes on the cell DNA.

Depending on the chemical composition of the pigments formed biochemically, a distinction is made between brownish-black eumelanin and reddish-yellow pheomelanin. The skin hue observed is determined by the ratio of these two types of melanin.

This pigment formation starting from the amino acid tyrosine is initiated predominantly by UVB radiation and is known as "indirect pigmentation". Its development runs over a number of days; the suntan obtained in this way lasts a few weeks. In the case of "direct pigmentation", which commences with the solar irradiation, predominantly colourless melanin precursors are oxidised by UVA radiation to dark-coloured melanin. Since this oxidation is reversible, it results in skin tanning which only lasts briefly.

Artificial tanning of the skin can be produced externally with the aid of make-up and orally by taking carotenoids.

Much more popular, however, is artificial tanning of the skin which can be achieved by the application of so-called self-tanners.

These compounds have, as a chemical structural feature, keto or aldehyde groups in the vicinity of alcohol functions and predominantly belong to the class of substances of the sugars. Particularly frequently employed self-tanning substances are 1,3-dihydroxyacetone (DHA), which is used in an amount of 700 t/a, and erythrulose.

Self-tanners can be reacted with the proteins and amino acids of the horny layer of the skin in the sense of a Maillard reaction or via a Michael addition, where polymers which give the skin a brownish hue form via a reaction route which has not yet been clarified completely. This reaction is complete after about 4 to 6 hours. The tan achieved in this way cannot be washed off and is only removed with the normal skin desquamation.

However, these coloured products do not themselves have UV-absorbent properties, meaning that additional sun protection (clothing, hat, UV filter) is necessary on exposure to the sun. In contrast to "sun-tanned" skin, skin tanned in this way is not protected against sunburn.

There therefore continues to be a demand for dermatologically tolerated skin-colouring substances which are suitable for use in cosmetic and/or dermatological preparations or medical products and which enhance the natural tanning of the skin by increasing melanin synthesis and at the same time enable better inherent skin protection or sun protection, in particular against UVB radiation.

The object on which the present invention is based therefore consisted in the provision of novel self-tanning substances having improved properties.

Surprisingly, it has now been found that certain chromen-4-one derivatives (chromone derivatives) are suitable as self-tanning compounds.

For the purposes of the invention, the term self-tanning active compound is used synonymously with self-tanning substance or self-tanner substance.

Similar applications of structurally related compounds are known from the literature:

Preparations for topical use which comprise chromone derivatives, such as, for example, chromone, 7-hydroxychromone, 7-methoxychromone, 5,7-dihydroxy-2-methylchromone, 3-methyl-2-butenyloxychromone, 3-acetyl-5,7-dihydroxy-2-methylchromone, 5-hydroxychromone, n-pentyl 7-methoxychromone-2-carboxylate, n-undecyl 5-methoxychromone-2-carboxylate, 5-hydroxy-7-methoxy-2-methylchromone, 7-methoxychromone-2-carboxylic acid, n-pentyl-chromone-2-carboxylic acid, 5-methoxychromone and chromone-2-carboxylic acid, are known from Japanese Patent Application JP 05/301813. The chromone derivatives act as skin-tolerated tyrosinase inhibitors which reduce hyperpigmentation of the skin.

Japanese Patent Application JP 09/188,608 discloses the use of substituted chromone derivatives, such as, in particular, 5,7-dihydroxychromones, 7-methoxychromones, 5-hydroxy-7-methoxy-2-methylchromone and 5-hydroxy-2-methylchromone, as active compound against grey hair. The action here is attributed to activation of the cells which form coloured pigments and the increase in melanogenesis. The generic formula disclosed in this Japanese application also encompasses chromone derivatives which have short acyloxy groups having 1 to 5 C atoms at position 7. In the course of the present invention, however, it was possible to show that 5-hydroxy-7-acetyl-2-methylchromone has no tanning activity in the ex vivo experiment.

WO 2007/087956 A1 describes chromone derivatives which have an alkoxy or hydroxyl group at position 7 and have a tanning activity.

The application US 2010/0158829 A1 discloses the use of various chromone derivatives for changing the colour of the skin, in particular for lightening the skin by inhibiting melanin transfer from the melanosomes to the keratinocytes.

The present invention therefore relates firstly to compounds of the formula I

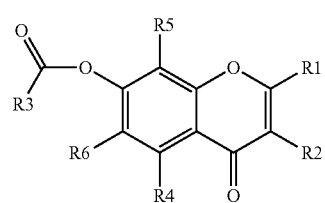

where

R1 and R2 stand, independently of one another, for

H,

OH, straight-chain or branched O—($C_1$- to $C_6$-alkyl) or straight-chain or branched $C_1$- to $C_6$-alkyl, where R1 and/or R2 may be substituted by one or more OH groups and/or where one or more non-adjacent $CH_2$ groups may be replaced by O;

R3 stands for straight-chain or branched $C_6$- to $C_{20}$-alkyl group, straight-chain or branched $C_2$- to $C_{20}$-alkenyl group, straight-chain or branched $C_2$- to $C_{20}$-alkynyl group, a cycloalkyl or cycloalkenyl group having 3 to 6 C atoms, or a radical of the formula III

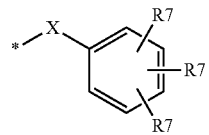

in which X stands for a straight-chain or branched $C_1$- to $C_6$-alkylene or straight-chain or branched $C_2$- to $C_6$-alkenylene and the radicals R7 are selected, independently of one another, from H, OH, straight-chain or branched $C_1$- to $C_6$-alkyl or straight-chain or branched O—($C_1$- to $C_6$-alkyl), R4 stands for H, OH or straight-chain or branched O—($C_1$- to $C_{20}$-alkyl), R5 and R6 stand, independently of one another, for

H,

OH, straight-chain or branched $C_1$- to $C_{20}$-alkyl group, straight-chain or branched $C_2$- to $C_{20}$-alkenyl group, straight-chain or branched $C_1$- to $C_{20}$-hydroxyalkyl group, where the hydroxyl group may be bonded to a primary or secondary carbon atom of the chain and/or one or more non-adjacent $CH_2$ groups may be replaced by O, or straight-chain or branched O—($C_1$- to $C_{20}$-alkyl) group.

In the sense of the present invention, the term "compound of the formula I" basically also encompasses the salts of the respective compounds of the formula I. The preferred salts here include, in particular, alkali metal and alkaline-earth metal salts, zinc salts and ammonium salts, but in particular sodium salts and potassium salts.

R1 preferably stands for H, OH, $OCH_3$, $CH_3$, $CH_2OH$ or $CH_2OCH_3$. R1 particularly preferably stands for $CH_2OCH_3$, $CH_2OH$ or $CH_3$, very particularly preferably for $CH_3$.

R2 in formula I preferably stands for H, OH, $OCH_3$, $CH_3$, $CH_2OH$ or $CH_2OCH_3$. R2 particularly preferably stands for H, OH or $OCH_3$, very particularly preferably for H.

R3 preferably stands for straight-chain or branched $C_6$- to $C_{20}$-alkyl group, straight-chain or branched $C_2$- to $C_{20}$-alkenyl group, or a radical of the formula III

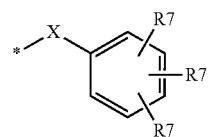

in which X stands for a straight-chain or branched $C_1$- to $C_6$-alkylene or straight-chain or branched $C_2$- to $C_6$-alkenylene and the radicals R7 are selected, independently of one another, from H, OH, straight-chain or branched $C_1$- to $C_6$-alkyl or straight-chain or branched O—($C_1$- to $C_6$-alkyl).

In the radical of the formula III, X preferably stands for —$CH_2$—, —$CH_2CH_2$—, —CH=CH—, —$CH_2$—CH=CH— or —CH=CH—$CH_2$—, particularly preferably for —$CH_2CH_2$— or —CH=CH—. R7

R3 is very particularly preferably selected from the group comprising

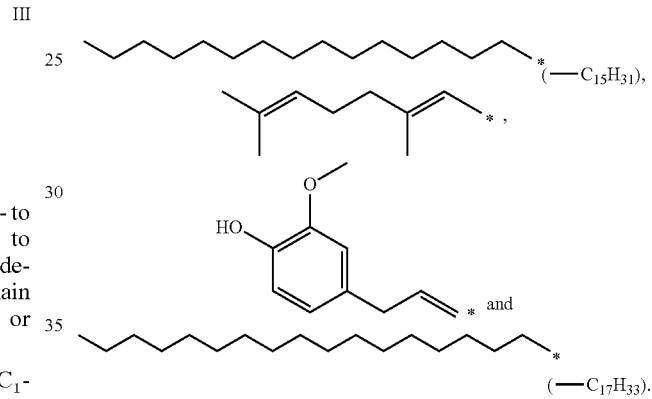

R4 preferably stands for H, OH or a straight-chain or branched $C_1$- to $C_6$-alkyl group, particularly preferably for OH or $OCH_3$, very particularly preferably for OH.

R5 preferably stands for H or OH, particularly preferably for H.

R6 preferably stands for H or OH, particularly preferably for H.

The radicals R7 are preferably selected, independently of one another, from H, OH and $OCH_3$, particularly preferably one radical R7 stands for H, one radical R7 stands for OH and one radical R7 stands for $OCH_3$.

In a preferred embodiment of the present invention, the compound of the formula I stands for a compound of the formula II

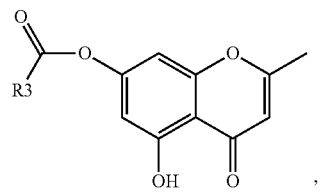

in which R3 is defined as described above.

The compound of the formula I is particularly preferably selected from the compounds of the formula Ia, Ib, Ic and Id

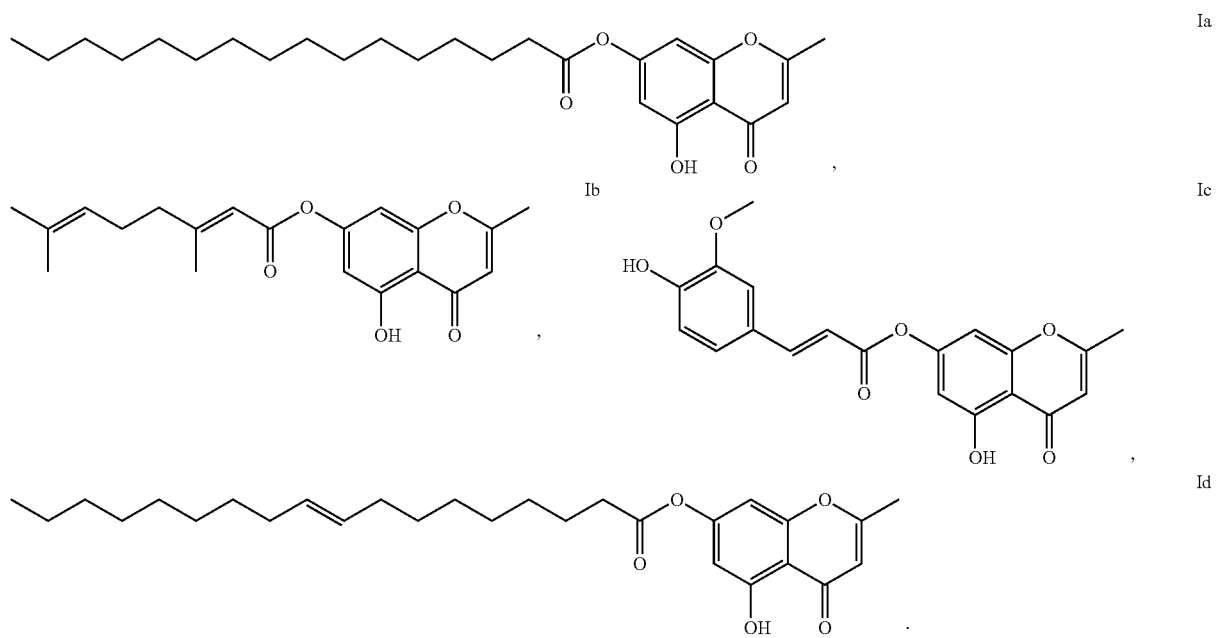

Very particular preference is given to compounds of the formula Ia.

The compounds of the formula I according to the invention, as defined above, can be obtained by cyclisation of a correspondingly substituted o-hydroxyacetophenone using an anhydride or using an acyl chloride under basic conditions. The acyl groups, i.e. on the one hand O-acyl groups formed by reaction of the free hydroxyl group with the anhydride or acyl chloride, on the other hand C-acyl groups in position 3 of the chromone system, can subsequently be removed. The reaction can be carried out analogously to Kelly, T; Kim M. H.; *J. Org. Chem.* 1992, 57, 1593-97.

Further derivatives of the formula I can be obtained by conventional reactions on the ring system or derivatisation of the functional groups. The reaction condition necessary for this purpose for such reactions, such as, for example, oxidations, reductions, transesterifications, etherifications, is easily found by a person skilled in the art for syntheses of this type in the generally available literature on organic reactions.

The ester function in position 7 of the chromone system can be introduced here by a simple esterification reaction.

The present invention therefore furthermore also relates to a process for the preparation of a compound of the formula I as defined above, characterised in that an o-hydroxyacetophenone of the formula IV

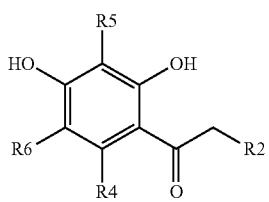

where the substituents R2 to R6 have one of the meanings described above or described as preferred, is cyclised using acetyl chloride under basic conditions, and the product is subsequently reacted with a compound of the formula R3-COCl in an esterification reaction.

The cyclisation is preferably carried out in a solvent selected from the group tetrahydrofuran, diethyl ether, diisopropyl ether, methyl ter-butyl ether or 1,4-dioxane.

The cyclisation is preferably carried out under inert-gas conditions. $K_2CO_3$ or another reagent from the group KO-tBu (potassium tert-butoxide), LiOH, KOH or DBU is advantageously introduced into pyridine at temperatures between $-10°$ C. and $35°$ C., preferably at room temperature. The actual reaction temperature is between $-10$ and $175°$ C., preferably between 35 and $100°$ C. The reaction is particularly preferably carried out at $50°$ C. or $66°$ C.

In the sense of the present invention, a straight-chain or branched alkyl group having 1 to 6 C atoms is, for example, methyl, ethyl, isopropyl, propyl, butyl, sec-butyl or tert-butyl, pentyl, isopentyl, 1-, 2- or 3-methylbutyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, 1,1-, 1,2-, 1,3-, 2,2-, 2,3- or 3,3-dimethylbutyl, f- or 2-ethylbutyl, 1-, 2-, 3- or 4-methylpentyl or hexyl.

Besides the radicals listed above, an alkyl radical having 1 to 20 C atoms can also be, for example, heptyl, 1-ethylpentyl, octyl, 1-ethylhexyl, nonyl, decyl, undecyl, dodecyl, tridecyl, tetradecyl, pentadecyl, hexadecyl, heptadecyl, octadecyl, nonadecyl or eicosyl.

An alkyl radical having 6 to 20 C atoms is taken to mean the same radicals as described, but where the radicals methyl, ethyl, isopropyl, propyl, butyl, sec-butyl or tert-butyl, pentyl, isopentyl, 1-, 2- or 3-methylbutyl, 1,1-, 1,2- or 2,2-dimethylpropyl and 1-ethylpropyl are excluded from the above list.

A $C_1$- to $C_6$-alkylene radical is, for example, methylene, ethylene, propylene, butylene, pentylene or hexylene.

In accordance with the invention, an alkenyl group may contain one or more double bonds. A branched or unbranched alkenyl group having 2 to 20 C atoms is, for example, allyl, vinyl, propenyl, 2- or 3-butenyl, isobutenyl, sec-butenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl, isopentenyl, hexenyl, heptenyl or octenyl, —$C_9H_{17}$, —$C_{10}H_{19}$ to —$C_{20}H_{39}$.

Examples of a $C_2$- to $C_6$-alkenylene radical are ethenylene, propenylene, 2- or 3-butenylene, 1-, 2-, 3- or 4-pentenylene or hexenylene.

An alkynyl radical may contain one or more triple bonds. Examples of a branched or unbranched alkynyl group having 2 to 20 C atoms are ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$.

A cycloalkyl or cycloalkenyl group in the sense of the present invention contains 3 to 6 C atoms. Cycloalkenyl groups contain one or two double bonds. Examples of cylclalkyl or cylclalkenyl groups having 3 to 6 C atoms are cyclopropyl, -butyl, -pentyl or -hexyl, furthermore also cyclopentenyl, -hexenyl or -hexadienyl.

The compounds of the formula I can be employed in self-tanning products as self-tanning substance and/or for increasing melanin synthesis in the skin, for improving melanin transport and/or for improving the distribution of melanin in suprabasal layers and/or for protecting the skin against damaging UV rays.

The present invention therefore furthermore relates to the use of a compound of the formula I, as described above, as self-tanning substance.

The present invention likewise relates to the use of a compound of the formula I, as described above, for increasing melanin synthesis, improving melanin transport and/or improving the distribution of melanin in suprabasal layers.

Compounds of the formula I increase melanin synthesis and improve melanin transport from the melanocytes to the keratinocytes. This has an effect on the colour of the skin and causes a tanning effect.

Besides the tanning action, the compounds of the formula I may also have an antioxidant action and are well tolerated by the skin. In addition, preferred compounds of those described here are colourless or only weakly coloured and thus do not result in discoloration of the preparations, or only do so to a small extent. In addition, the preferred compounds have improved solubility in cosmetic oils.

In order that the compounds of the formula I are able to develop their positive action on the skin particularly well, it may be preferred to allow the compounds of the formula I, as described above, to penetrate into deeper skin layers. A number of possibilities are available to this end. Firstly, the compounds of the formula I may have adequate lipophilicity in order to be able to penetrate through the outer skin layer into epidermal layers. As a further possibility, corresponding transport means, for example liposomes, which enable transport of the compounds of the formula I through the outer skin layers, may also be provided in the preparation. Finally, systemic transport of the compounds of the formula I is also conceivable. The preparation is then formulated, for example, in such a way that it is suitable for oral administration.

The use according to the invention preferably takes place non-therapeutically.

The present invention furthermore relates to a preparation comprising at least one compound of the formula I or preferred embodiments thereof, defined as described above.

The preparations here are usually preparations which can be applied topically, for example cosmetic or dermatological formulations or medical products. In this case, the preparations comprise a cosmetically or dermatologically suitable vehicle and, depending on the desired property profile, optionally further suitable ingredients. In the case of pharmaceutical preparations, the preparations in this case comprise a pharmaceutically tolerated vehicle and optionally further pharmaceutical active compounds.

In the sense of the present invention, the term composition or formulation is also used synonymously alongside the term preparation.

"Can be applied topically" in the sense of the invention means that the preparation is used externally and locally, i.e. that the preparation must be suitable for, for example, application to the skin.

The preparations may include or comprise, essentially consist of or consist of the said requisite or optional constituents. All compounds or components which can be used in the preparations are either known and commercially available or can be synthesised by known processes.

The preparation is preferably a cosmetic or pharmaceutical preparation; the preparation is particularly preferably a cosmetic preparation.

The at least one compound of the formula I is employed in the preparations according to the invention in amounts of 0.01 to 10% by weight, preferably in amounts of 0.05 to 10% by weight, particularly preferably in amounts of 0.1% by weight to 5% by weight and very particularly preferably in amounts of 0.5 to 2% by weight, based on the total amount of the preparation. The person skilled in the art is presented with absolutely no difficulties here in selecting the amounts appropriately depending on the intended action of the preparation.

Furthermore, the preparations according to the invention may comprise at least one further self-tanning substance as further ingredient. This can be either a self-tanner which reacts with the amino acids of the skin in the sense of a Maillard reaction or via a Michael addition, or a so-called melanogenesis promoter or propigmentation active compound which promotes the natural tanning of the skin. Advantageous self-tanning substances which can be employed are, inter alia: 1,3-dihydroxyacetone, glycerolaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone). Very particular preference is given to 1,3-dihydroxyacetone, erythrulose or a combination thereof. Propigmentation substances can in principle be all active compounds known to the person skilled in the art. Examples thereof are glycyrrhetinic acid, melanocyte-stimulating hormone (alpha-MSH), peptide analogues, thymidine dinucleotides, L-tyrosine and esters thereof or bicyclic monoterpenediols (described in Brown et al., Photochemistry and Photobiology B: Biology 63 (2001) 148-161).

The at least one further self-tanning substance is preferably present in the preparation in an amount of 0.01 to 20% by weight, particularly preferably in an amount of 0.5 to 15% by weight and very particularly preferably in an amount of 1 to 8% by weight, based on the total amount of the preparation.

Preparations having self-tanner properties, in particular those which comprise dihydroxyacetone, tend towards malodours on application to the human skin, which are thought to be caused by degradation products of dihydroxyacetone itself or by products of side reactions and which are regarded as unpleasant by some users. It has been found that these malodours are prevented on use of formaldehyde scavengers and/or flavonoids. The preparation according to the invention may therefore preferably also comprise formaldehyde scavengers and optionally flavonoids for improving the odour.

The preparation according to the invention, which combines a self-tanning substance and a chromone of the formula I, has the following advantages over a self-tanning product without addition of chromone:

acceleration of the tanning reaction,
extension of the tanning reaction owing to the indirect tanning reaction (UV-free tanning extension),
intensification of the tanning reaction,
prevention of uneven tanning due to inexpert application,
the tanning achieved comes close to natural tanning,
improvement in protection against UV radiation.

Besides the compounds of the formula I, the preparations according to the invention may additionally also comprise at least one UV filter.

Organic UV filters, so-called hydrophilic or lipophilic sun-protection filters, which are effective in the UVA region and/or UVB region and/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO-93/04665. Further examples of organic filters are indicated in the patent application EP-A 0 487 404. The said UV filters are usually named below in accordance with INCI nomenclature.

Particularly suitable for a combination are:

para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed under the name "Uvinul P25" by BASF.

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", "Uvinul N539" from BASF, Etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidene-dicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzo-triazolyl)tetramethylbutylphenol in solid form, for example marketed by Fairmount Chemical under the name "MIXXIM BB/100", or in micronised form as an aqueous dispersion, for example marketed by BASF under the name "Tinosorb M".

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl 4'-aminobenzalmalonate)-s-triazine or 2,4,6-tris(biphenyl)-1,3,5-triazine. marketed as Tinosorb A2B by BASF, 2,2'-[6-(4-methoxyphenyl)-1,3,5-triazine-2,4-diyl]bis[5-(2-ethylhexyl)oxy]phenol, marketed as Tinosorb S by BASF, N2,N4-bis[4-[5-(1,1-dimethylpropyl)-2-benzoxazolyl]phenyl]-N6-(2-ethylhexyl)-1,3,5-triazine-2,4,6-triamine marketed as Uvasorb K 2A by Sigma 3V.

Anthraniline derivatives: Menthyl anthranilate, for example marketed by Symrise under the name "Neo Heliopan MA".

Imidazole derivatives: Ethylhexyldimethoxybenzylidenedioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl)benzoxazol-2-yl(4-phenyl)imino]-6-(2-ethylhexyl)imino-1,3,5-triazine, for example marketed by Sigma 3V under the name Uvasorb K2A, and mixtures comprising this.

Piperazine derivatives, such as, for example, the compound

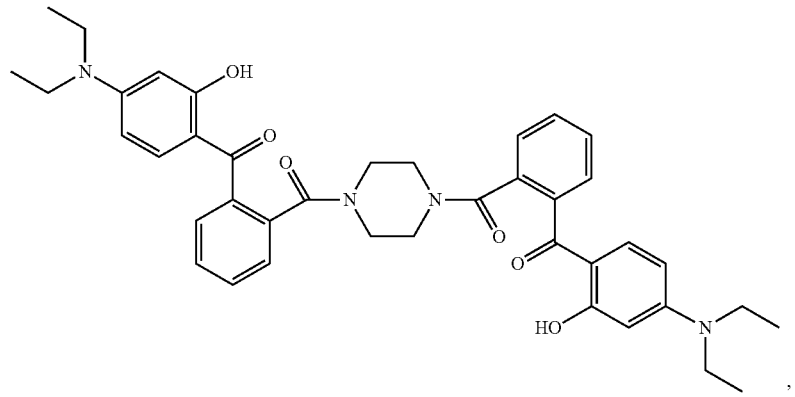 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

or the UV filters of the following structures

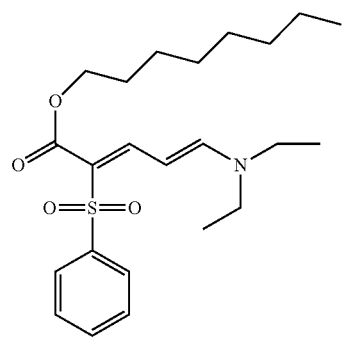

or

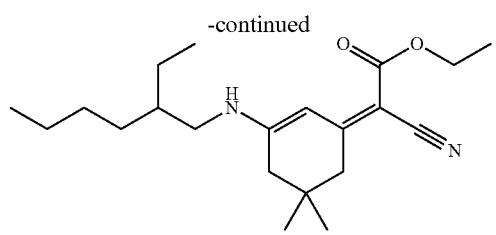

It is also possible to use UV filters based on polysiloxane copolymers having a random distribution in accordance with the following formula, where, for example, a=1,2; b=58 and c=2,8:

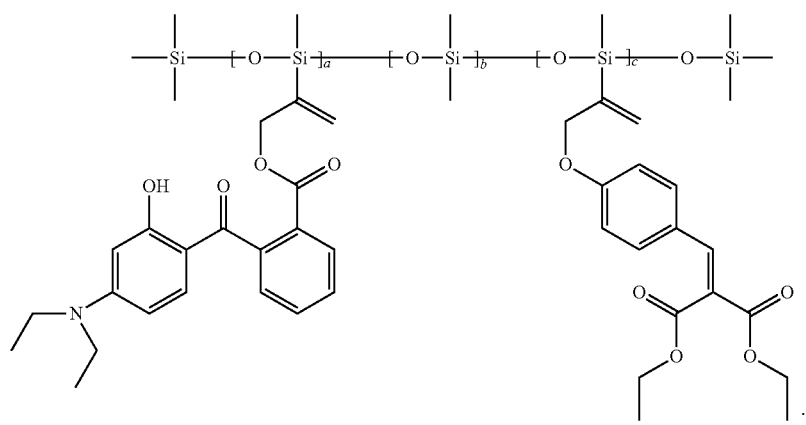 [SMILES: C=C(COC(=O)c1ccccc1C(=O)c1ccc(N(CC)CC)cc1O)[Si](C)(O[Si](C)(C)C)O[Si](C)(C)O[Si](C)(O[Si](C)(C)C)C(=C)COc1ccc(C=C(C(=O)OCC)C(=O)OCC)cc1]

The compounds listed should only be regarded as examples. It is of course also possible to use other UV filters.

Suitable organic UV-protecting substances can preferably be selected from the following list: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidene-dicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-bis[5-1 (dimethylpropyl)benzoxazol-2-yl(4-phenyl)imino]-6-(2-ethylhexyl)imino-1,3,5-triazine and mixtures thereof.

These organic UV filters are generally incorporated into formulations in an amount of 0.01 percent by weight to 20 percent by weight, preferably 1% by weight-10% by weight.

Besides the compounds of the formula I and the optional organic UV filters, as described above, the preparations may comprise further inorganic UV filters, so-called particulate UV filters.

These combinations with particulate UV filters are possible both as powder and also as dispersion or paste of the following types.

Preference is given here both to those from the group of the titanium dioxides, such as, for example, coated titanium dioxide (for example Eusolex® T-2000, Eusolex®T-AQUA, Eusolex®T-AVO, Eusolex®T-OLEO), zinc oxides (for example Sachtotec®), iron oxides or also cerium oxides and/or zirconium oxides.

Furthermore, combinations with pigmentary titanium dioxide or zinc oxide are also possible, where the particle size of these pigments are greater than or equal to 200 nm, for example Hombitan® FG or Hombitan® FF-Pharma.

It may furthermore be preferred for the preparations to comprise inorganic UV filters which have been aftertreated by conventional methods, as described, for example, in Cosmetics & Toiletries, February 1990, Vol. 105, pp. 53 64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanol-amines, silicon dioxide, aluminium oxide, further metal oxides, phosphates, such as sodium hexametaphosphate, or glycerine.

Particulate UV filters which are preferably employed here are:

untreated titanium dioxides, such as, for example, the products Microtitanium Dioxide MT 500 B from Tayca; titanium dioxide P25 from Degussa, Aftertreated micronised titanium dioxides with aluminium oxide and silicon dioxide aftertreatment, such as, for example, the product "Microtitanium Dioxide MT 100 SA from Tayca; or the product "Tioveil Fin" from Uniqema, Aftertreated micronised titanium dioxides with aluminium oxide and/or aluminium stearate/laurate aftertreatment, such as, for example, Microtitanium Dioxide MT 100 T from Tayca, Eusolex T-2000 from Merck, Aftertreated micronised titanium dioxides with iron oxide and/or iron stearate aftertreatment, such as, for example, the product "Microtitanium Dioxide MT 100 F" from Tayca, Aftertreated micronised titanium dioxides with silicon dioxide, aluminium oxide and silicone aftertreatment, such as, for example, the product "Microtitanium Dioxide MT 100 SAS", from Tayca, Aftertreated micronised titanium dioxides with sodium hexametaphosphates, such as, for example, the product "Microtitanium Dioxide MT 150 W" from Tayca.

The treated micronised titanium dioxides employed for the combination may also be aftertreated with:

octyltrimethoxysilanes; such as, for example, the product Tego Sun T 805 from Degussa, silicon dioxide; such as, for example, the product Parsol T-X from DSM, aluminium oxide and stearic acid; such as, for example, the product UV-Titan M160 from Sachtleben, aluminium and glycerine; such as, for example, the product UV-Titan from Sachtleben, aluminium and silicone oils, such as, for example, the product UV-Titan M262 from Sachtleben, sodium hexametaphosphate and polyvinylpyrrolidone, polydimethylsiloxanes, such as, for example, the product 70250 Cardre UF TiO2SI3" from Cardre,
polydimethylhydrogenosiloxanes, such as, for example, the product Microtitanium Dioxide USP Grade Hydrophobic" from Color Techniques.

The combination with the following products may furthermore also be advantageous:

Untreated zinc oxides, such as, for example, the product Z-Cote from BASF (Sunsmart), Nanox from Elementis aftertreated zinc oxides, such as, for example, the following products:
"Zinc Oxide CS-5" from Toshibi (ZnO aftertreated with polymethyl-hydrogenosiloxanes)
Nanogard Zinc Oxide FN from Nanophase Technologies
"SPD-Z1" from Shin-Etsu (ZnO aftertreated with a silicone-grafted acrylic polymer, dispersed in cyclodimethylsiloxanes
"Escalol Z100" from ISP (aluminium oxide-aftertreated ZnO dispersed in an ethylhexyl methoxycinnamate/ PVP-hexadecene/methicone copolymer mixture)
"Fuji ZNO-SMS-10" from Fuji Pigment (ZnO aftertreated with silicon dioxide and polymethylsilesquioxane);
Untreated cerium oxide micropigment, for example with the name
"Colloidal Cerium Oxide" from Rhone Poulenc
Untreated and/or aftertreated iron oxides with the name Nanogar from Arnaud.

By way of example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide. zinc oxide mixtures, such as, for example, the product UV-Titan M261 from Sachtleben.

These inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form.

The capsules in preparations to be employed in accordance with the invention are preferably present in amounts which ensure that the encapsulated UV filters are present in the preparation in the percent by weight ratios indicated above.

The preparations described, which in accordance with the invention comprise the at least one compound of the formula I, may furthermore also comprise coloured pigments, where the layer structure of the pigments is not limited.

The coloured pigment should preferably be skin-coloured or brownish on use of 0.5 to 5% by weight. The selection of a corresponding pigment is familiar to the person skilled in the art.

Preferred preparations may likewise comprise at least one further cosmetic active compound, for example selected from antioxidants, anti-ageing, anti-wrinkle, anti-dandruff, anti-acne, anti-cellulite active compounds, deodorants or vitamins.

The protective action of preparations against oxidative stress or against the effect of free radicals can be improved if the preparations comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA, pentasodium ethylenediamine tetramethylene phosphonate and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, α-glucosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Suitable antioxidants are also compounds of the formulae A or B

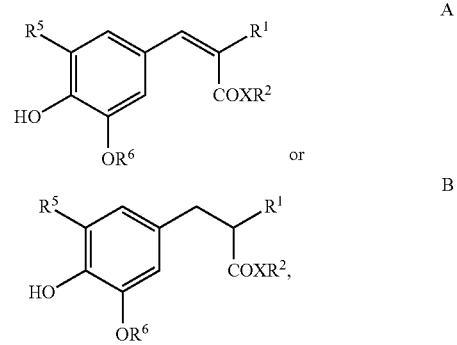

in which
R$^1$ can be selected from the group —C(O)CH$_3$, —CO$_2$R$^3$, —C(O)NH$_2$ and —C(O)N(R$^4$)$_2$,
X denotes O or NH,
R$^2$ denotes linear or branched alkyl having 1 to 30 C atoms,
R$^3$ denotes linear or branched alkyl having 1 to 20 C atoms,
R$^4$ in each case, independently of one another, denotes H or linear or branched alkyl having 1 to 8 C atoms,
R$^5$ denotes H, linear or branched alkyl having 1 to 8 C atoms or linear or branched alkoxy having 1 to 8 C atoms and
R$^6$ denotes linear or branched alkyl having 1 to 8 C atoms,
preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-di-methoxybenzyl)malonate (for example RonaCare® AP).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such preparations with the compounds according to the invention in percent by weight ratios in the range from 1000:1 to 1:1000, preferably in percent by weight ratios of 100:1 to 1:100.

Of the phenols which can be used in accordance with the invention, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3'4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers and I. M. C. M. Rietjens (Free Radical Biology & Medicine 2001, 31(7), 869-881, have investigated the pH dependence of the antioxidant action of hydroxyflavones. Quercetin exhibits the highest activity amongst the structures investigated over the entire pH range.

Suitable anti-ageing active compounds, in particular for skin-care preparations, are preferably so-called compatible solutes. These are substances which are involved in the osmosis regulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myoinositol, mannitol or sorbitol, and/or one or more of the osmolytically active substances mentioned below: taurine, choline, betaine, phosphorylcholine, glycero-phosphorylcholines, glutamine, glycine, α-alanine, glutamate, aspartate, proline and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidinecarboxylic acids (such as ectoin and hydroxyectoin), proline, betaine, glutamine, cyclic diphosphoglycerate, N.-acetylornithine, trimethylamine N-oxide di-myoinositol phosphate (DIP), cyclic 2,3-diphosphoglycerate (cDPG), 1,1-diglycerol phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof.

Additionally, anti-aging active compounds which can be used are products from Merck, such as, for example, 5,7-dihydroxy-2-methylchromone, marketed under the trade name RonaCare® Luremine, RonaCare® Isoquercetin, RonaCare® Tilirosid or RonaCare® Cyclopeptide 5.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or preparations in ranges from 0.01 to 5.0% by weight, based on the total weight. Nutrition-physiological applications are oriented towards the respective recommended vitamin requirement.

The retinoids described are at the same time also effective anti-cellulite active compounds. A likewise known anti-cellulite active compound is caffeine.

The present invention also relates to a process for the preparation of a preparation, as described above, characterised in that at least one compound of the formula I is mixed with a vehicle which is suitable for topical preparations and optionally with assistants and or fillers. Suitable vehicles and assistants or fillers are described in detail in the following part.

The said constituents of the preparation can be incorporated in the usual manner, with the aid of techniques which are well known to the person skilled in the art.

The cosmetic and dermatological preparations can be in various forms. Thus, they can be, for example, a solution, a water-free preparation, an emulsion or microemulsion of the water-in-oil (W/O) type or of the oil-in-water (O/W) type, a multiple emulsion, for example of the water-in-oil-in-water (W/O/W) or O/W/O type, a gel, a solid stick, an ointment or also an aerosol. Preference is given to emulsions. O/W emulsions are particularly preferred. Emulsions, W/O emulsions and O/W emulsions can be obtained in the usual manner.

The following, for example, may be mentioned as application form of the preparations to be employed: solutions, suspensions, emulsions, PIT emulsions, pastes, ointments, gels, creams, lotions, powders, soaps, surfactant-containing cleansing preparations, oils, aerosols plasters, compresses, bandages and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, XTend 226 (L'Oréal), glycerol fatty acid esters, polyethylene glycols and fatty acid esters of sorbitan, or mixtures of these substances.

A preferred solubiliser in general is 2-isopropyl-5-methyl-cyclohexanecarbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkyl-amidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

The lipid phase may advantageously be selected from the following group of substances:
  mineral oils, mineral waxes
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
  silicone oils, such as dimethylpolysiloxanes, diethylpolysiloxanes, diphenyl-polysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acid and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group branched and unbranched hydrocarbons and hydrocarbon waxes, silicone oils, dialkyl ethers, the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may, for example, advantageously be selected from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as sole lipid component of the oil phase.

The aqueous phase of the preparations to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropyl-methylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

In a preferred embodiment, the preparations to be employed comprise hydrophilic surfactants. The hydrophilic surfactants are preferably selected from the group of the alkylglucosides, acyl lactylates, betaines and coconut amphoacetates.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R', or if isoalkyl derivatives are present, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laurethyl-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/cerinate, polyethylene glycol (20) glyceryl oleate, polyethylene glycol (20) glyceryl isostearate, polyethylene glycol (18) glyceryl oleate (cocoate).

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:
fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG-30 dipolyhydroxystearate.

The preparation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The dispersant or solubiliser used can be an oil, wax or other fatty bodies, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion which is in the form of a protective cream or milk and comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The preparation may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is generally made of the customary propellants, such as alkanes, fluoroalkanes and chlorofluoroalkanes, preferably alkanes.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference.

Further important features and advantages of the invention arise from the sub-claims and from the examples.

The examples are intended to explain the present invention in greater detail without restricting the scope thereof.

EXAMPLES

Example 1

Synthesis of 5-hydroxy-2-methyl-4-oxo-4H-chromen-7-yl hexadecanoate (Ia)

5,7-Dihydroxymethylchromone (15 g, 78 mmol) is dissolved in N,N-dimethylformamide (360 ml), and potassium tert-butoxide (9 g, 80 mmol) is added to the brown solution under a stream of nitrogen. The mixture is subsequently heated at 30° C. for 2.5 h. Palmitoyl chloride (24 ml, 79.5 mmol) in N,N-dimethylformamide (80 ml) is then slowly added dropwise to the solution at 30° C. The resultant suspension is stirred at 30° C. for a further 2 hours, and 400 ml of DI water are then added dropwise. After 1 hour, the solid is filtered off with suction via a suction filter, dried well by suction and dried at 40° C. in a vacuum drying cabinet.

Yield (after recrystallisation in ethanol): 22 g=66% of theory
Colour: beige
Empirical formula: $C_{26}H_{38}O_5$
Molecular weight: 430.6 g/mol
Analysis:
MS (EI): m/e (relative intensity, %)=430.2 ([M+] 25), 192.1 ([M+] 100).
1H-NMR (CDCl$_3$, 500 MHz): δ=12.28 (s, 1H, OH), 6.68 (d, 1H, J=2 Hz), 6.51 (d, 1H, J=2 Hz), 6.1 (s, 1H), 2.56 (t, 2H, J=7.5), 1.75 (m, 2H), 1.26 (m, 24H), 0.88 (t, 3H, J=6.7 Hz).

Example 2

Synthesis of 5-hydroxy-2-methyl-4-oxo-4H-chromen-7-yl(E)-3,7-dimethylocta-2,6-dienoate (Ib)

Compound Ib is prepared analogously to Example 1. 3,7-Dimethylocta-2,6-dienoyl chloride is employed instead of palmitoyl chloride.
Analysis:
Empirical formula: $C_{20}H_{22}O_5$
Molecular weight: 342.4 g/mol
MS (EI): m/e (relative intensity, %)=342 ([M+] 15), 69 ([M+] 100).
$^1$H-NMR (DMSO-$_6$, 300 MHz): δ=12.86 (s, 1H, OH), 6.9 (d, 1H), 6.62 (d, 1H), 6.35 (s, 1H), 5.93 (s, 1H), 5.11 (t, 1H), 2.40 (s, 3H), 2.26-2.17 (m, 7H), 1.67 (s, 3H), 1.60 (s, 3H).

Example 3

Synthesis of 5-hydroxy-2-methyl-4-oxo-4H-chromen-7-yl(E)-3-(4-hydroxy-3-methoxyphenyl) acrylate (Ic)

Compound Ic is prepared analogously to Example 1. 4-Hydroxy-3-methoxycinnamoyl chloride is employed instead of palmitoyl chloride.

Example 4

Synthesis of 5-hydroxy-2-methyl-4-oxo-4H-chromen-7-yl(E)-octadec-9-enoate (Id)

Compound Id is prepared analogously to Example 1. (E)-Octadec-9-enoyl chloride is employed instead of palmitoyl chloride.
Analysis:
Empirical formula: $C_{28}H_{40}O_5$
Molecular weight: 456.63 g/mol
MS (EI): m/e (relative intensity, %)=456 ([M+] 25), 192 ([M+] 100).
$^1$H-NMR (DMSO-$_6$, 500 MHz): δ=15.49 (s, 1H, OH), 6.78 (d, 1H), 6.57 (d, 1H), 6.23 (s, 1H), 5.38 (t, 2H), 2.59 (t, 2H), 2.38 (s, 3H), 2.04 (t, 4H), 1.71 (q, 2H), 1.45-1.22 (m, 20H), 0.86 (t, 3H)

Example 5

Ex Vivo Study on the Promotion of Melanogenesis

Preparation of the Tissue Samples
The tissue samples having a diameter of 10 mm are taken from the stomach tissue of a 32-year-old Caucasian woman and stored in BEM medium at 37° C. in a moist atmosphere having a $CO_2$ content of 5%. The tissue samples are employed in accordance with the following test plan:

| Sample | Topical application | UV | Number of tissue samples |
|---|---|---|---|
| Untreated skin (T0) | — | without | 3 |
| Untreated skin | — | without | 6 |
| Placebo | yes | without | 6 |
| Ia | yes | without | 6 |
| 5-Hydroxy-7-acetyl-2-methylchromen-4-one (comparative substance) | yes | without | 6 |
| 5-Hydroxy-7-methoxy-2-methylchromen-4-one (comparative substance) | yes | without | 6 |
| Untreated skin | — | with | 6 |
| Placebo | yes | with | 6 |
| Ia | yes | with | 6 |
| 5-Hydroxy-7-acetyl-2-methylchromen-4-one (comparative substance) | yes | with | 6 |
| 5-Hydroxy-7-methoxy-2-methylchromen-4-one (comparative substance) | yes | with | 6 |

Product Application
30 μl of test solution are placed on a filter paper and immediately laid on the tissue sample.
Irradiations
The irradiations are carried out daily before treatment of the tissue samples with test solutions. An RMX 3W Vilbert Lourmat instrument is used. The UV dose is 1.04 J/cm2 comprising 6/8% of UVB.
Sampling
On the first day (D0), 3 untreated tissue samples are halved, and in each case one half is fixed in buffered formalin solution. The respective other halves are frozen at −80° C.
Histological Analysis
After fixing for 24 hours in buffered formalin solution, the samples are dehydrated in a Leica TP1010 automatic dryer and impregnated with paraffin. After embedding with the aid of a Leica EG1160 station, 5 μm thin cross sections are produced from the samples using a Leica RM 2125 Minot-type microtome.
The cross sections are mounted on Superfrost Plus specimen slides made from silanised glass. The light-microscopy analysis is carried out by means of a Leica Orthoplan microscope with 25-times magnification in order to assess the general morphology or 40-times magnification in order to visualise the melanin.
General Morphology
The general morphology is assessed after staining of the paraffinised cross-sections in accordance with Masson's trichrome in the Goldner variant.
Melanin Visualisation
The melanin visualisation is carried out after impregnation of the paraffinised cross-sections with silver in accordance with Masson in the Fontana variant.
Chromatometry
The colour coordinates of the tissue samples are determined by means of a Minolta CM 2600d chromatometer.
Results
1) Test Series without UV Irradiation:

|  |  | L | % L |
|---|---|---|---|
| Untreated sample | D0 | 61.41 | |
|  | D10 | 62.22 | 1.3 |
| Sample treated with placebo | D0 | 61.68 | |
|  | D10 | 63.05 | 2.2 |
| Sample treated with compound Ia | D0 | 64.53 | |
|  | D10 | 61.24 | −5.1 |
| Sample treated with 5-hydroxy-7-acetyl-2-methylchromen-4-one | D0 | 62.19 | |
|  | D10 | 63.98 | 2.9 |

-continued

|  | L | % L |
|---|---|---|
| Sample treated with 5-hydroxy-7-methoxy-2-methylchromen-4-one | D0  61.50 | |
| | D10  64.64 | 5.1 |

Untreated Samples:

After treatment for 10 days, the melanocytes exhibit a moderate degree of dendritic branching and loading with melanin. The number of contacts with adjacent keratinocytes is low, as is the melanin transfer rate. The content of melanin in basal keratinocytes is moderate and low in suprabasal keratinocytes.

Samples Treated with Placebo:

The melanocytes exhibit low activity after treatment for 10 days. Melanin is clearly detectable in basal keratinocytes, the melanin content in suprabasal keratinocytes is low.

Samples Treated with Compound Ia:

The melanocytes exhibit very high activity after treatment for 10 days. Melanin is readily detectable in basal keratinocytes, the melanin content in suprabasal keratinocytes is moderate.

Sample Treated with 5-Hydroxy-7-Acetyl-2-Methyl-chromen-4-One:

The melanocytes exhibit very low activity together with a moderate melanin content in basal keratinocytes and a low content of melanin in suprabasal keratinocytes.

Sample Treated with 5-Hydroxy-7-Methoxy-2-Methyl-chromen-4-One

The melanocytes exhibit very low activity, associated with a moderate melanin content in basal keratinocytes and a low content of melanin in suprabasal keratinocytes.

Chromatometric Analysis:

Comparative measurements on the start day and after 10 days give the following results: in the case of the untreated samples, only slight changes can be observed after 10 days. Samples treated with placebo exhibit a moderate increase in the light/dark parameter L. For the samples treated with compound Ia, a decrease in the L parameter by 5.1% can be detected, which confirms the pro-pigmenting activity (compared with the untreated control, this corresponds to an increase of 43% of the area of the basal layer occupied by melanin). For samples treated with 5-hydroxy-7-acetyl-2-methylchromen-4-one or 5-hydroxy-7-methoxy-2-methylchromen-4-one, an increase in the L parameter by 2.9% and 5.1% respectively can be detected, which tends to indicate a skin-lightening activity.

2) Test Series with UV Irradiation:

|  | L | % L |
|---|---|---|
| Untreated sample | D0  65.87 | |
| | D10  64.56 | −2 |
| Sample treated with placebo | D0  65.45 | |
| | D10  65.41 | −0.1 |
| Sample treated with compound Ia | D0  64.07 | |
| | D10  61.52 | −4 |
| Sample treated with 5-hydroxy-7-acetyl-2-methylchromen-4-one | D0  63.66 | |
| | D10  64.87 | 1.9 |
| Sample treated with 5-hydroxy-7-methoxy-2-methylchromen-4-one | D0  63.63 | |
| | D10  64.60 | 1.5 |

Untreated Samples:

After treatment for ten days, the melanocytes exhibit a significant degree of dendritic branching and are clearly loaded with melanin. There are readily detectable contacts with adjacent keratinocytes and a moderate degree of melanin transfer. Melanin is clearly detectable in basal keratinocytes, while only a low melanin content can be detected in suprabasal keratinocytes.

Samples Treated with Placebo:

The melanocytes exhibit a high degree of activity. The melanin content is high in basal keratinocytes, low in suprabasal keratinocytes.

Samples Treated with Compound Ia:

The melanocytes exhibit a high degree of activity. The content of melanin is high in basal keratinocytes, moderate in suprabasal keratinocytes.

Sample Treated with 5-Hydroxy-7-Acetyl-2-Methyl-chromen-4-One:

The melanocytes exhibit low activity together with a moderate melanin content in basal keratinocytes and a low melanin content in suprabasal keratinocytes.

Sample Treated with 5-Hydroxy-7-Methoxy-2-Methyl-chromen-4-One

The melanocytes exhibit very low activity, which is associated with a moderate melanin content in basal keratinocytes and a low melanin content in suprabasal keratinocytes.

Chromatometric Analysis:

Comparative measurements on the start day and after 10 days give the following results: the untreated samples exhibit a decrease in the L parameter by 2.0% after 10 days. In the case of the samples treated with placebo, a slight increase in the L value by 2.2% can be observed. In the case of the samples treated with compound Ia, the light/dark parameter L drops by 4.0% in the investigation period. This documents a clear pro-pigmenting activity of compound Ia, in particular compared with the L value of the untreated samples. For samples treated with 5-hydroxy-7-acetyl-2-methylchromen-4-one or 5-hydroxy-7-methoxy-2-methylchromen-4-one, an increase in the L parameter can be detected, which tends to indicate a skin-lightening activity.

Example 6

O/W Formulation

| Constituents/trade name | Source of supply | INCI | [% by wt.] |
|---|---|---|---|
| A | | | |
| Marlipal 1618/11 | (1) | CETEARETH-11 | 3 |
| Lanette O | (2) | CETEARYLALCOHOL | 7 |
| Luvitol EHO | (3) | CETEARYLOCTANOATE | 5 |
| Tegosoft TN | (4) | C12-15 ALKYLBENZOATE | 2.5 |
| Miglyol 812 N | (1) | CAPRYLIC/CAPRIC TRIGLYCERIDE | 2.5 |
| Propyl 4-hydroxybenzoate | (5) | PROPYLPARABEN | 0.05 |
| 5-Hydroxy-2-methyl-4-oxo-4H-chromen-7-yl hexadecanoate (Ia) | | | 0.5 |
| B | | | |
| 1,2-Propanediol | (5) | PROPYLENE GLYCOL | 4 |
| Methyl 4-hydroxybenzoate | (5) | METHYLPARABEN | 0.15 |
| Water, demineralised | | AQUA (WATER) | to 100 |
| Water, demineralised | | | 10 |
| Total | | | 100.00 |

Preparation Process:

Firstly, phase A is warmed to 75° C. and phase B to 80° C. Phase B is then slowly added to phase A with stirring and stirred until a homogeneous mixture forms.

Sources of Supply:
(1) Sasol Germany GmbH (2) Cognis GmbH (3) BASF AG (4) Degussa-Goldschmidt AG (5) Merck KGaA/Rona®

Example 7

O/W Formulation

| Constituents/trade name | Source of supply | INCI | [% by wt.] |
|---|---|---|---|
| A | | | |
| Marlipal 1618/11 | (1) | CETEARETH-11 | 3 |
| Lanette O | (2) | CETEARYLALCOHOL | 7 |
| Luvitol EHO | (3) | CETEARYLOCTANOATE | 5 |
| Tegosoft TN | (4) | C12-15 ALKYLBENZOATE | 2.5 |
| Miglyol 812 N | (1) | CAPRYLIC/CAPRIC TRIGLYCERIDE | 2.5 |
| Propyl 4-hydroxybenzoate | (5) | PROPYLPARABEN | 0.05 |
| 5-Hydroxy-2-methyl-4-oxo-4H-chromen-7-yl (E)-3,7-dimethylocta-2,6-dienoate (Ib) | | | 0.1 |
| B | | | |
| 1,2-Propanediol | (5) | PROPYLENE GLYCOL | 4 |
| Methyl 4-hydroxybenzoate | (5) | METHYLPARABEN | 0.15 |
| Water, demineralised | | AQUA (WATER) | to 100 |
| Water, demineralised | | | 10 |
| Total | | | 100.00 |

Preparation Process:
Firstly, phase A is warmed to 75° C. and phase B to 80° C. Phase B is then slowly added to phase A with stirring and stirred until a homogeneous mixture forms.
Sources of Supply:
(1) Sasol Germany GmbH (2) Cognis GmbH (3) BASF AG (4) Degussa-Goldschmidt AG (5) Merck KGaA/Rona®

Example 8

O/W Formulation

| Constituents/trade name | Source of supply | INCI | [% by wt.] |
|---|---|---|---|
| A | | | |
| Tego Care 150 | (1) | GLYCERYL STEARATE, STEARETH-25, CETETH-20, STEARYL ALCOHOL | 8 |
| Lanette O | (2) | CETEARYL ALCOHOL | 1.5 |
| Luvitol EHO | (3) | CETEARYL OCTANOATE | 5 |
| Miglyol 812 N | (4) | CAPRYLIC/CAPRIC TRIGLYCERIDE | 5 |
| Paraffin liquid | (5) | PARAFFINUM LIQUIDUM (MINERAL OIL) | 3 |

-continued

| Constituents/trade name | Source of supply | INCI | [% by wt.] |
|---|---|---|---|
| AbilWax 2434 | (1) | STEAROXY DIMETHICONE | 1.6 |
| Dow Corning 200 Fluid (350 cs) | (6) | DIMETHICONE | 0.5 |
| Propyl 4-hydroxybenzoate | (5) | PROPYLLPARABEN | 0.05 |
| B | | | |
| 1,2-Propanediol | (5) | PROPYLENE GLYCOL | 3 |
| Methyl 4-hydroxybenzoate | (5) | METHYLPARABEN | 0.15 |
| Water, demineralised | | AQUA (WATER) | to 100 |
| C | | | |
| Probiol L 05018 (empty liposomes) | (7) | AQUA, ALCOHOL DENAT, LECITHIN, GLYCERINE, DISODIUM PHOSPHATE | 5 |
| Water, demineralised | | AQUA (WATER) | 10.00 |
| 5-Hydroxy-2-methyl-4-oxo-4H-chromen-7-yl (E)-3-(4-hydroxy-3-methoxyphenyl)acrylate (Ic) | | | 0.2 |
| Total | | | 100.00 |

Preparation Process:
Firstly, phases A and B are warmed to 80° C. Phase B is then slowly added to phase A with stirring and homogenised. The mixture is then cooled, and phase C is added at 40° C.
Sources of Supply:
(1) Degussa-Goldschmidt AG, (2) Cognis GmbH, (3) BASF AG, (4) Sasol Germany GmbH, (5) Merck KGaA/Rona®, (6) Dow Corning, (7) Kuhs GmbH & Co. KG

Example 9

W/O Formulation

| Constituents/trade name | Source of supply | INCI | [% by wt.] |
|---|---|---|---|
| A | | | |
| Dow Corning 3225 C | (1) | CYCLOMETHICONE, DIMETHICONE COPOLYOL | 23.6 |
| Propyl 4-hydroxybenzoate | (2) | PROPYLPARABEN | 0.05 |
| 5-Hydroxy-2-methyl-4-oxo-4H-chromen-7-yl (E)-3,7-dimethylocta-2,6-dienoate (Ib) | | | 0.1 |
| B | | | |
| Methyl 4-hydroxybenzoate | (2) | METHYLPARABEN | 0.15 |
| 1,2-Propanediol | (2) | PROPYLENE GLYCOL | 35.9 |
| Water, demineralised | | AQUA (WATER) | to 100 |
| Total | | | 100.00 |

Preparation Process:
Firstly, phase B is dissolved and then added to phase A. The pH is adjusted to the value pH=6.0 using sodium hydroxide solution or citric acid.
Sources of Supply:
(1) Dow Corning (2) Merck KGaA/Rona®

Example 10

O/W Anti-Ageing Cream with UV A/B Protection

| Constituents/trade name | Source of supply | INCI | [% by wt.] |
|---|---|---|---|
| A | | | |
| Eusolex ® 2292 | (1) | ETHYLHEXYL METHOXYCINNAMATE, BHT | 3 |
| Eusolex ® 4360 | (1) | BENZOPHENONE-3 | 0.5 |
| Tego Care 150 | (2) | GLYCERYL STEARATE, STEARETH-25, CETETH-20, STEARYL ALCOHOL | 8 |
| Lanette O | (3) | CETEARYL ALCOHOL | 1.5 |
| Luvitol EHO | (4) | CETEARYL OCTANOATE | 5 |
| Miglyol 812 N | (5) | CAPRYLIC/CAPRIC TRIGLYCERIDE | 5 |
| Paraffin liquid | (1) | PARAFFINUM LIQUIDUM (MINERAL OIL) | 3 |
| Abil-Wax 2434 | (2) | STEAROXY DIMETHICONE | 1.6 |
| Dow Corning 200 Fluid (350 cs) | (6) | DIMETHICONE | 0.5 |
| Propyl 4-hydroxybenzoate | (1) | PROPYLPARABEN | 0.05 |
| 5-Hydroxy-2-methyl-4-oxo-4H-chromen-7-yl hexadecanoate (Ia) | | | 1 |
| B | | | |
| 1,2-Propanediol | (1) | PROPYLENE GLYCOL | 3 |
| Methyl 4-hydroxybenzoate sodium salt | (1) | SODIUM METHYLPARABEN | 0.17 |
| Water, demineralised | | AQUA (WATER) | to 100 |
| Total | | | 100.00 |

Preparation Process:

Firstly, phases A and B are mixed separately and warmed to 80° C. Phase B is then slowly added to phase A with stirring. The mixture is homogenised cooled to room temperature.

Sources of Supply:

(1) Merck KGaA/Rona®, (2) Degussa-Goldschmidt AG, (3) Cognis GmbH, (4) BASF AG, (5) Sasol Germany GmbH, (6)

The invention claimed is:

1. A compound of formula I

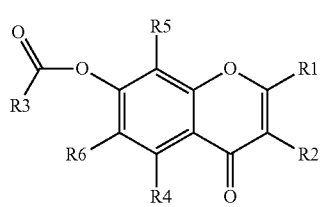

where
R1 and R2 stand, independently of one another, for
H,
OH,
straight-chain or branched O—($C_1$- to $C_6$-alkyl) or
straight-chain or branched $C_1$- to $C_6$-alkyl,
where R1 and/or R2 may be substituted by one or more OH groups
and/or where one or more non-adjacent $CH_2$ groups may each be replaced by O;
R3 stands for
straight-chain or branched $C_6$- to $C_{20}$-alkyl group,
straight-chain or branched $C_2$- to $C_{20}$-alkenyl group,
straight-chain or branched $C_2$- to $C_{20}$-alkynyl group,
a cycloalkyl or cycloalkenyl group having 3 to 6 carbon atoms, or
a radical of the formula III

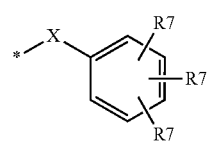

in which X stands for a straight-chain or branched $C_1$- to $C_6$-alkylene or straight-chain or branched $C_2$- to $C_6$-alkenylene and the radicals R7 are selected, independently of one another, from H, OH, straight-chain or branched $C_1$- to $C_6$-alkyl or straight-chain or branched O—($C_1$- to $C_6$-alkyl),
R4 stands for H, OH or straight-chain or branched O—($C_1$- to $C_{20}$-alkyl),
R5 and R6 stand, independently of one another, for
H,
OH,
straight-chain or branched $C_1$- to $C_{20}$-alkyl group,
straight-chain or branched $C_2$- to $C_{20}$-alkenyl group,
straight-chain or branched $C_1$- to $C_{20}$-hydroxyalkyl group, where the hydroxyl group may be bonded to a primary or secondary carbon atom of the chain and/or one or more non-adjacent $CH_2$ groups may be replaced by O, or
straight-chain or branched O—($C_1$- to $C_{20}$-alkyl) group.

2. A compound according to claim 1, wherein R1 stands for H, OH, $OCH_3$, $CH_3$, $CH_2OH$ or $CH_2OCH_3$.

3. A compound according to claim 1, wherein R2 stands for H, OH, $OCH_3$, $CH_3$, $CH_2OH$ or $CH_2OCH_3$.

4. A compound according to claim 1, wherein R3 stands for straight-chain or branched $C_6$- to $C_{20}$-alkyl group, straight-chain or branched $C_2$- to $C_{20}$-alkenyl group, or a radical of the formula III

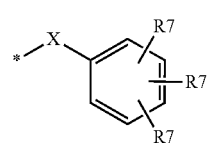

in which X stands for a straight-chain or branched $C_1$- to $C_6$-alkylene or straight-chain or branched $C_2$- to $C_6$-alkenylene and the radicals R7 are selected, independently of one another, from H, OH, straight-chain or branched $C_1$- to $C_6$-alkyl or straight-chain or branched O—($C_1$- to $C_6$-alkyl).

5. A compound according to claim 1, wherein R4 stands for H, OH or a straight-chain or branched $C_1$- to $C_6$-alkyl group.

6. A compound according to claim 1, wherein R5 and R6 stand, independently of one another, for H or OH.

7. A compound according to claim 1, wherein R3 stands for
straight-chain or branched $C_6$- to $C_{20}$-alkyl group,
straight-chain or branched $C_2$- to $C_{20}$-alkenyl group,
straight-chain or branched $C_2$- to $C_{20}$-alkynyl group, or
a cycloalkyl or cycloalkenyl group having 3 to 6 carbon atoms.

8. A compound according to claim 1, wherein said compound is of formula II

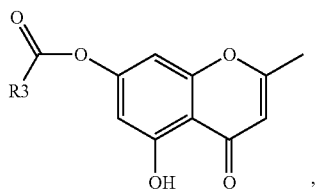

in which R3 is as defined in claim 1.

9. A process for preparation of a compound according to claim 1, said process comprising:
cyclizing an o-hydroxyacetophenone of formula IV

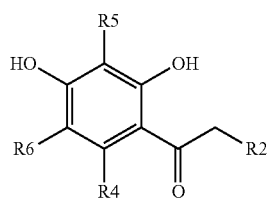

where the substituents R2 to R6 are as defined in claim 1, using acetyl chloride under basic conditions, and
subsequently reacting the resultant product with a compound of the formula R3-COCl in an esterification reaction, in which R3 is as defined in claim 1.

10. A method of self-tanning comprising applying a compound according to claim 1 as a self-tanning substance.

11. A method for increasing melanin synthesis, improving melanin transport and/or improving the distribution of melanin in suprabasal layers, comprising applying a compound according to claim 1.

12. A composition comprising at least one compound according to claim 1, and a vehicle which is suitable for topical application.

13. The composition according to claim 12, wherein said composition contains said at least one compound in an amount of 0.01 to 10% by weight.

14. The composition according to claim 12, wherein said composition further comprises at least one further self-tanning substance.

15. A process for preparing a composition according to claim 12, said process comprising mixing said at least one compound with a vehicle which is suitable for topical application.

16. A compound according to claim 1, wherein R1 stands for $CH_2OCH_3$, $CH_2OH$ or $CH_3$.

17. A compound according to claim 1, wherein R2 stands for H, OH or $OCH_3$.

18. A compound according to claim 1, wherein X stands for —$CH_2$—, —$CH_2CH_2$—, —CH=CH—, —$CH_2$—CH=CH— or —CH=CH—$CH_2$—.

19. A compound according to claim 1, wherein R3 is selected from;

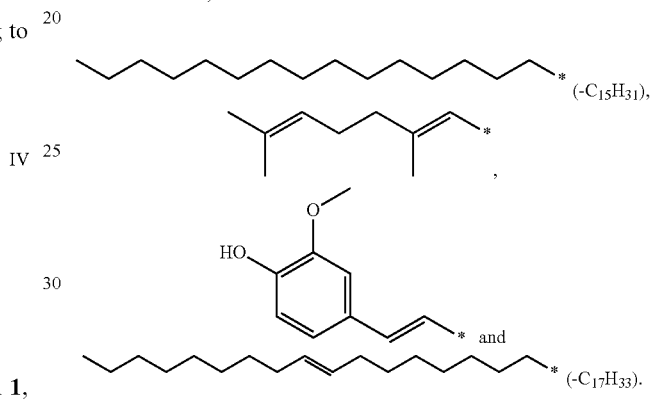

20. A compound according to claim 1, wherein R4 stands for OH or $OCH_3$.

21. A compound according to claim 1, wherein R5 and R6 are each H.

22. A compound according to claim 1, wherein R7 is, in each case independently, H, OH or $OCH_3$.

23. A compound according to claim 1, wherein one radical R7 stands for H, one radical R7 stands for OH, and one radical R7 stands for $OCH_3$.

24. A compound according to claim 1, wherein said compound is selected from compounds of formula Ia to Id

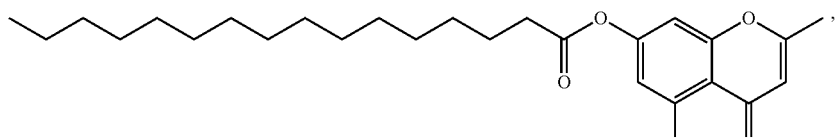

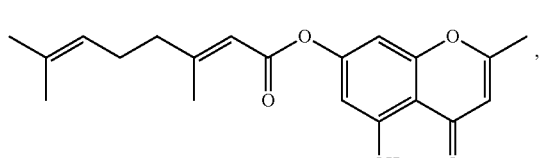

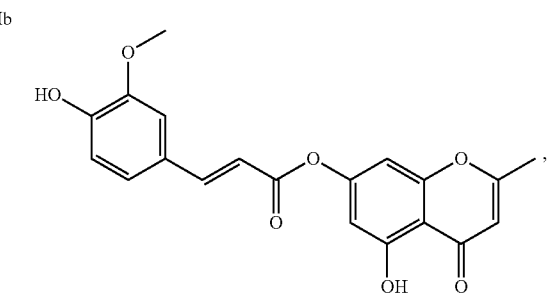

-continued
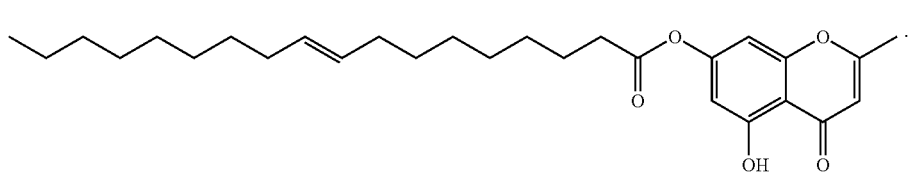
10
25. A compound according to claim 24, wherein said compound is of formula Ia
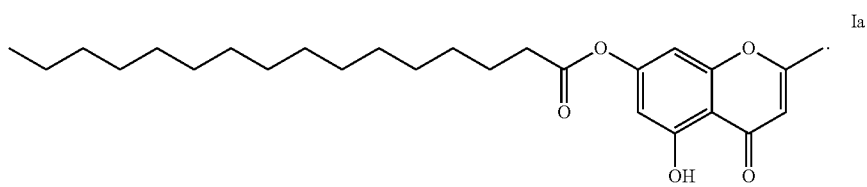 [SMILES: CCCCCCCCCCCCCCCC(=O)Oc1cc(O)c2c(=O)cc(C)oc2c1]
* * * * *